United States Patent
Tazaki et al.

(10) Patent No.: US 8,415,157 B2
(45) Date of Patent: Apr. 9, 2013

(54) CELL CULTURE CONTAINER AND CELL CULTURE METHOD

(75) Inventors: Go Tazaki, Ibaraki (JP); Tomoko Kosaka, Ibaraki (JP); Motohiro Fukuda, Ibaraki (JP)

(73) Assignee: KURARAY Co., Ltd., Kurashiki-shi (JP)

( * ) Notice: Subject to any disclaimer, the term of this patent is extended or adjusted under 35 U.S.C. 154(b) by 0 days.

(21) Appl. No.: 13/229,087

(22) Filed: Sep. 9, 2011

(65) Prior Publication Data

US 2011/0318829 A1 Dec. 29, 2011

Related U.S. Application Data

(62) Division of application No. 12/665,474, filed as application No. PCT/JP2008/060943 on Jun. 16, 2008.

(30) Foreign Application Priority Data

Jun. 18, 2007 (JP) .................................. 2007-160158

(51) Int. Cl.
*C12N 5/02* (2006.01)
*C12N 5/00* (2006.01)
*C12N 5/071* (2010.01)
*C12M 1/00* (2006.01)
*C12M 1/22* (2006.01)

(52) U.S. Cl.
USPC ........ 435/383; 435/305.2; 435/366; 435/370; 435/385; 435/395

(58) Field of Classification Search .................. 435/383, 435/385, 305.2, 366, 370, 395
See application file for complete search history.

(56) References Cited

U.S. PATENT DOCUMENTS

| | | |
|---|---|---|
| 2006/0281172 A1 | 12/2006 | Kuwabara et al. |
| 2007/0202589 A1 | 8/2007 | Kikuchi et al. |
| 2009/0017540 A1 | 1/2009 | Nishio et al. |
| 2009/0075363 A1 | 3/2009 | Morimoto et al. |
| 2009/0075366 A1 | 3/2009 | Tazaki et al. |
| 2009/0170190 A1 | 7/2009 | Nishi et al. |
| 2010/0190253 A1 | 7/2010 | Tazaki et al. |
| 2010/0331216 A1 | 12/2010 | Sokabe et al. |
| 2011/0045500 A1 | 2/2011 | Taniguchi et al. |

FOREIGN PATENT DOCUMENTS

| | | |
|---|---|---|
| JP | 2004 154027 | 6/2004 |
| JP | 2006 191809 | 7/2006 |

(Continued)

OTHER PUBLICATIONS

Machine translation into English of Nishi et al. (WO 2007/049576).*

*Primary Examiner* — Nathan Bowers
*Assistant Examiner* — Gautam Prakash
(74) *Attorney, Agent, or Firm* — Oblon, Spivak, McClelland, Maier & Neustadt, L.L.P.

(57) ABSTRACT

A cell culture chamber and a cell culture method that are capable of effectively constructing an intercellular network in a culture space are provided. A cell culture chamber (10) according to the present invention is a cell culture chamber (10) including a plurality of microchambers (11) formed on a surface thereof, characterized in that convex portions (side walls 12) that partition the microchambers (11) adjacent to each other are formed to prevent cells from being adhered to upper surfaces of the convex portions. Consequently, cells can be cultured exclusively within the microchambers (11), and an intercellular network can be constructed effectively.

11 Claims, 7 Drawing Sheets

FOREIGN PATENT DOCUMENTS

| | | |
|---|---|---|
| JP | 2006 325532 | 12/2006 |
| WO | 2006 075597 | 7/2006 |
| WO | 2007 049576 | 5/2007 |
| WO | WO 2007/049576 | 5/2007 |

* cited by examiner

CELL CULTURE CONTAINER AND CELL CULTURE METHOD

TECHNICAL FIELD

The present invention relates to a cell culture chamber and a cell culture method.

BACKGROUND ART

A technique of using cells isolated from a tissue in testing or examination is an essential method in the biotechnology-related fields. It is widely used in diagnosing a disease or pathological condition, searching for a new drug and evaluating the efficacy of a drug, or in animal inspection, plant inspection, testing for environmental pollutants, and so on. Thus, cells and the like used in the biotechnology field have been greatly diversified.

The isolated cells are sometimes used immediately for testing, but in many cases, the cells are cultured in a culture dish or a test tube. Various examinations are carried out using the cultured cells. Cell lines in culture for use in cell culture tests are required to show drug susceptibility and toxic reaction that are similar to those obtained in a test performed in a living body, that is, a so-called in vivo test. In short, it is necessary to be able to construct an intercellular network regularly arranged on the surface of a cell culture chamber. The intercellular network herein described refers to a state where cells can be connected with each other and interact with each other, a form in which cells are accumulated to form a cell mass, or a form in which cells are formed in a net shape. Furthermore, the cell lines in culture for use in cell culture tests are extremely expensive, so an improvement in survival rate and proliferation rate of cells is desired.

The cell culture tests measure the effect of a drug or the like to be evaluated, by changing its amount, concentration, and the like under the same conditions. For this reason, it is necessary that the cell culture chambers be identical in material, shape, and the like. As the cell culture chambers, a petri dish made of plastic, a petri dish made of glass, a glass plate fixed into a chamber, a well plate, and the like are generally used. Examples of the well plate include 6-well, 12-well, 48-well, and 96-well plates or petri dishes. In general, these plates have substantially the same overall size. As the number of wells increases, the size of a single well becomes smaller. A single well corresponds to a single culture dish. With the recent trend toward miniaturization, a 384-well plate having a number of culture dishes with a small diameter has also come to be used. Bottom surfaces of these culture dishes have a flat plate shape, and each of the bottom surfaces is used as a culture surface.

However, the use of the conventional cell culture chamber for culturing tissue cells causes the cells to be thinned into a form with no orientation. Additionally, the cells are randomly arranged on the surface of the cell culture chamber, so intercellular networks cross each other in a complicated manner. This causes a problem of being incapable of reproducing cell functions in vivo.

As methods for solving the above-mentioned problem and culturing cells in three dimensions, there are disclosed a method for culturing cells utilizing a cell culture chamber having a size on the order of several hundreds of μm (see Patent Document 1), a method for culturing cells utilizing micropatterns including a cell placement section and a flow channel (see Patent Document 2), and the like.

[Patent Document 1] Japanese Unexamined Patent Application Publication No. 2004-154027
[Patent Document 2] Japanese Unexamined Patent Application Publication No. 2006-191809

DISCLOSURE OF INVENTION

Technical Problem

In both Patent Documents 1 and 2, convex portions for partitioning a space for culturing cells are formed. In Patent Document 1, however, the width of the upper surface of each convex portion is about twice or three times the size of a cell. This causes a problem that cells are adhered to the upper surface and an intercellular network is not constructed effectively in a culture space. On the other hand, in Patent Document 2, the width of each convex portion is smaller than the size of a cell, but the height of each convex portion is lower. This causes a problem that cells run on the convex portions and an intercellular network is not constructed effectively in the culture space.

The present invention has been made to solve the above-mentioned problems, and therefore has an object to provide a cell culture chamber and a cell culture method that are capable of effectively constructing an intercellular network in a culture space.

Technical Solution

A cell culture chamber according to the present invention is a cell culture chamber including a plurality of microchambers formed on a surface thereof, characterized in that convex portions that partition the microchambers adjacent to each other are formed to prevent cells from being adhered to upper surfaces of the convex portions. The convex portions may have a multi-stage structure to prevent cells from being adhered to an upper surface of each stage. Further, it is preferable that the upper surfaces of the convex portions have a short side width of 0.5 to 15 μm and the convex portions have a height equal to or more than three times the short side width. The convex portions preferably have a height of 30 to 300 μm.

Further, in 50% or more of an upper portion in a height direction of the side walls with a horizontal plane of each of the microchambers as a reference surface, an angle formed between the horizontal plane and each side surface of the side walls is preferably 80° to 90°.

Further, each of the microchambers preferably has a bottom surface area of $6.25 \times 10^{-4}$ mm$^2$ to 0.563 mm$^2$. In the case where cultured cells are liver cells, a major axis of the bottom surface is preferably 1 to 1.5 times a minor axis thereof. Meanwhile, in the case of evaluating migration properties of cells, the major axis of the bottom surface is preferably 1.5 to 50 times the minor axis thereof.

Furthermore, it is preferable that the microchambers communicate with at least one adjacent microchamber and an opening therefor have a bottom surface width of 1 μm to 25 μm.

Further, it is preferable that an area having the microchambers formed therein be subjected to surface treatment and an integrated layer film formed by the surface treatment have two or more layers including at least one layer of an inorganic film and at least one layer of an organic film. Moreover, the area is preferably transparent.

A cell culture method according to the present invention is a method for injecting cells into the microchambers formed in the cell culture chamber, and for culturing the cells in the above-mentioned cell culture chamber. The cells are preferably selected from liver cells, fat cells, osteoblasts, pulp cells, cartilage cells, stem cells, nerve cells, and cardiac muscle cells.

ADVANTAGEOUS EFFECTS

According to the present invention, it is possible to provide a cell culture chamber and a cell culture method that are capable of effectively constructing an intercellular network in a culture space.

EXPLANATION OF REFERENCE

10 CELL CULTURE CHAMBER
11 MICROCHAMBER
12 SIDE WALL
121 FIRST SIDE WALL
122 SECOND SIDE WALL
13 OPENING

BEST MODES FOR CARRYING OUT THE INVENTION

A cell culture chamber according to the present invention has a concave-convex pattern, i.e., a plurality of microchambers or culture spaces formed therein. The width and height of side walls (convex portions) for partitioning the microchambers are optimized, thereby making it possible to culture cells exclusively within the microchambers and construct an intercellular network effectively.

The dimensions of the microchambers each surrounded by the side walls have to be set within the optimum range for culturing cells. If the bottom surface area of each microchamber is too large, cells are thinly elongated and fail to show a three-dimensional structure, as in the culture on a flat plate. If, on the other hand, the bottom surface area of each microchamber is too small, it cannot accommodate cells. Accordingly, the dimensions of the space structure are preferably in a range capable of containing one or a plurality of cells according to cell species to be cultured. In the case of forming a cell mass in which a plurality of cells is accumulated, the dimensions are preferably in a range capable of containing the cell mass.

It is also necessary to set the side walls of the microchambers within the optimum range for culturing cells. If the width of each side wall is too large, cells are adhered to the upper surface of the side wall, and thus such side wall is unsuitable for culture. If the width of each side wall is too small, the production thereof becomes difficult. If the height of each side wall is too low, cells run on the side wall, and thus such side wall is unsuitable for culture. If the height of each side wall is too high, the production thereof is difficult and material diffusion becomes difficult, leading to a deterioration of the culture environment.

In addition, openings are formed in the side walls to obtain a structure in which the plurality of microchambers communicates with each other, thereby making it possible to supply oxygen and nutrients to cells and remove waste products from the cells effectively. Note that the height of the side walls, the dimensions of the microchambers, and the width of the openings are appropriately set according to cell species to be cultured, thereby enabling application to various culture systems.

Hereinafter, embodiments of the present invention will be described. Note that the present invention is not limited to embodiments described below. To clarify the explanation, the following description and the drawings are simplified as appropriate.

Embodiments

Figure 1:
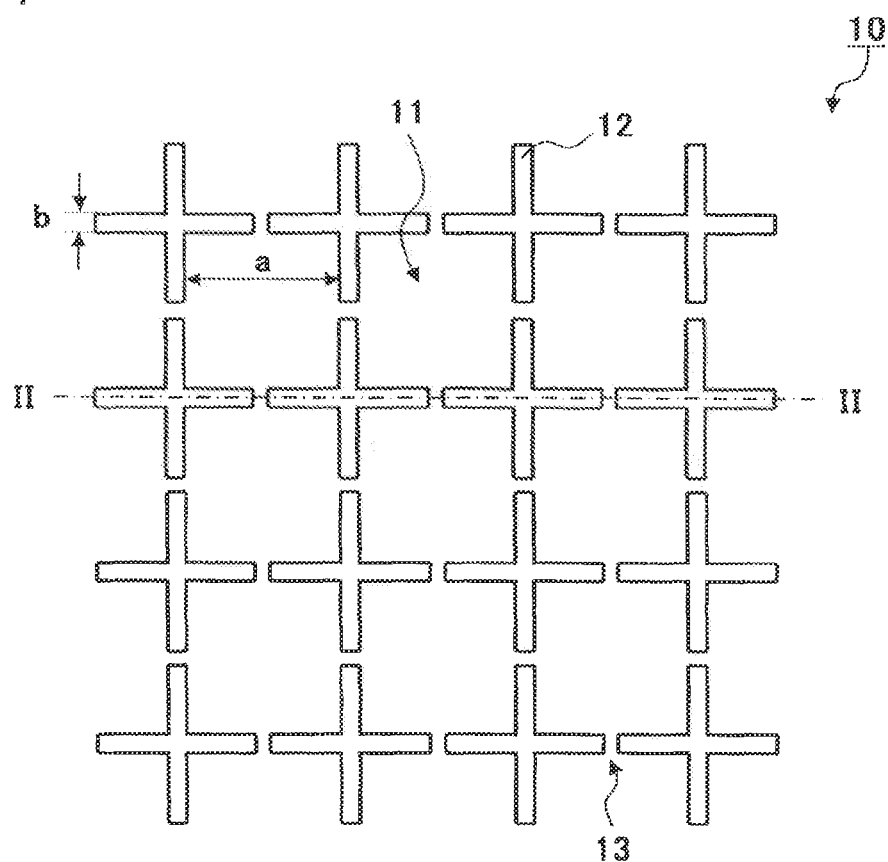
FIG. 1 is a plane view showing the structure of a cell culture chamber according to an embodiment of the present invention.
Figure 2:
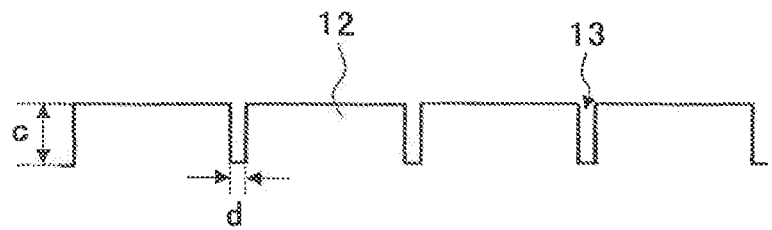
FIG. 2 is a sectional view showing the structure of the cell culture chamber according to an embodiment of the present invention.

The structure of a cell culture chamber according to an embodiment of the present invention will be described with reference to FIGS. 1 and 2. FIG. 1 is a plane view showing the structure of the cell culture chamber according to this embodiment, and FIG. 2 is a sectional view taken along the line II-II of FIG. 1. As shown in FIG. 1, a cell culture chamber 10 includes microchambers 11, side walls 12, and openings 13. The plurality of side walls 12 is formed in a net shape on the culture surface of the cell culture chamber 10, and spaces surrounded by the side walls 12 correspond to the microchambers 11. Additionally, each of the openings 13 is formed at a central portion of each side of the side walls 12 which are formed on four sides of each of the microchambers 11 having a rectangle shape.

FIG. 1 shows a width "a" of the bottom surface of each of the microchambers 11, a width "b" and a height "c" of each of the side walls 12 for partitioning the microchambers 11, and a width "d" of each of the openings 13 for allowing communication between the microchambers 11 adjacent to each other. Here, it is necessary that $0.5\ \mu m \leq b \leq 15\ \mu m$ and $c/b \geq 3$ be satisfied. If the height "b" of each of the side walls 12 exceeds 15 μm, cells are adhered to the upper surfaces of the side walls, and thus such side walls are unsuitable for culture. If, on the other hand, the width "b" of each of the side walls 12 is less than 0.5 μm, the production thereof becomes difficult.

If the height of each of the side walls is too low, cells run on the side walls, and thus such side walls are unsuitable for culture. If the height "c" of each of the side walls 12 is less than twice the width "b" of each of the side walls 12, cells to be cultured in the microchambers 11 run on the side walls and move to the adjacent microchambers 11. Additionally, the height "c" of each of the side walls 12 is preferably within a range of 30 μm to 300 μm. Specifically, in the case of forming a cell mass having an equivalent diameter of 100 μm, the height "c" of each of the side walls 12 is preferably 50 μm to 150 μm. Here, if the height "c" of each of the side walls is too high, the production thereof is difficult and material diffusion becomes difficult, leading to a deterioration of the culture environment. The side walls 12 may have a multi-stage shape.

The bottom surface shape of each of the microchambers 11 is not particularly limited, and various shapes other than a square, a circle, and a polygon can be employed. This bottom surface area is preferably $6.25 \times 10^{-4}$ mm$^2$ to 0.563 mm$^2$. Specifically, in cell culture for reproducing a liver function in vivo, this bottom surface area is preferably 0.01 mm$^2$ to 0.1 mm$^2$. In this case, the major axis of the bottom surface is preferably 1 to 1.5 times the minor axis thereof. An isotropic shape is more preferably used. If a square is employed, for example, in the case of forming a cell mass having an equivalent diameter of 100 μm, the length of one side thereof is preferably 100 μm to 300 μm.

Further, in the culture for orienting nerve cells in order to reproduce a neural network in vivo, a microchamber having a rectangle shape and an opening can be employed. For example, it is preferable that the short-side width of the microchamber be 20 μm and the length of the long side thereof be equal to or greater than 100 μm. That is, the major axis of the bottom surface is preferably equal to or more than five times the minor axis thereof.

In the case of evaluating migration properties of cells in order to examine the functions of cells in vivo, a rectangle shape can be employed. For example, it is preferable that the short side width of the microchamber be 15 μm and the length of the long side thereof be 22.5 to 750 μm. That is, the major axis of the bottom surface is preferably 1.5 to 50 times the minor axis thereof.

An angle formed between the horizontal plane and the side wall 12 of each of the microchambers 11 should be set to an angle at which cells are prevented from running on the microchambers. Accordingly, 50% or more of an upper portion of a side surface preferably has an angle of 80 to 90°, and more preferably, 85° to 90°.

Figure 3:
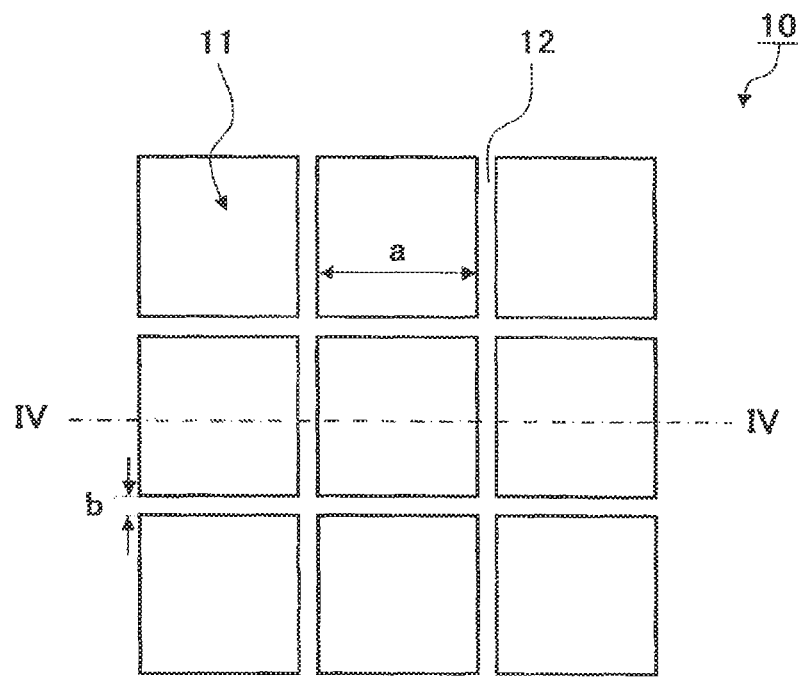
FIG. 3 is a plane view showing the structure of a cell culture chamber according to an embodiment of the present invention.
Figure 4:
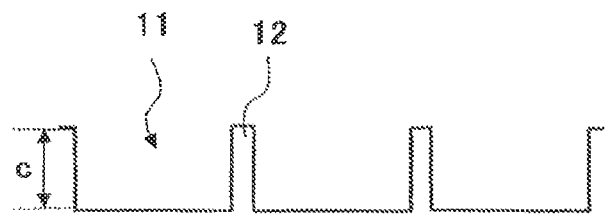
FIG. 4 is a sectional view showing the structure of the cell culture chamber according to an embodiment of the present invention.
Figure 11:
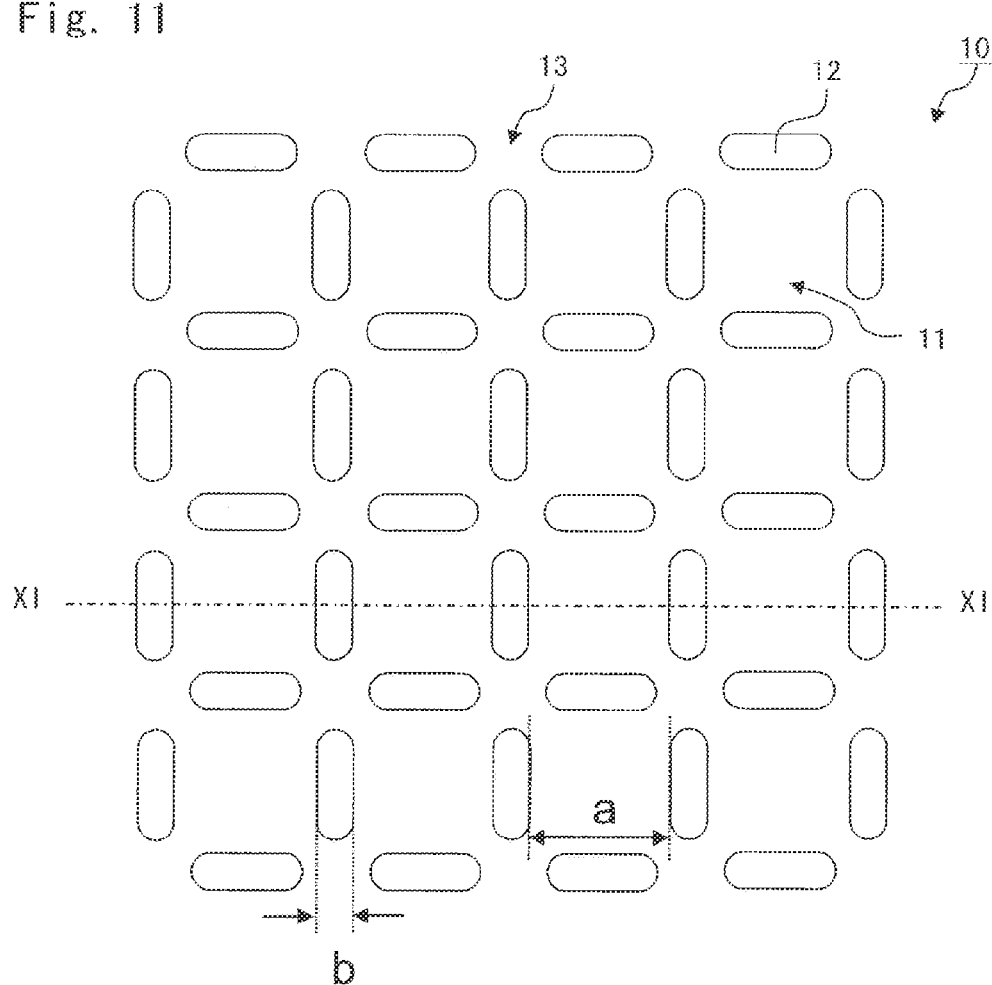
FIG. 11 is a plane view showing the structure of a cell culture chamber according to an embodiment of the present invention.
Figure 12:
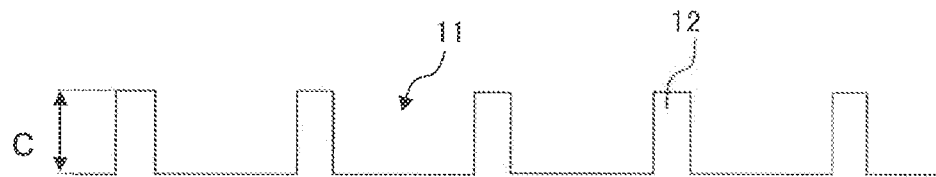
FIG. 12 is a sectional view showing the structure of the cell culture chamber according to an embodiment of the present invention.

The width "d" of each of the openings 13 for allowing communication between the microchambers 11 adjacent to each other is preferably set to a width in which cells are prevented from moving from the microchamber 11, in which the cultured cell is first seeded, to the adjacent microchamber 11. When the equivalent diameter of the cultured cell is 20 μm, for example, the width is preferably 5 to 15 μm. In addition, like the concave-convex pattern shown in FIGS. 11 and 12, each of the openings 13 is not necessarily formed at the center of each of the microchambers 11, but may be formed at a corner portion (corner portion of a rectangular). Here, FIG. 11 is a plane view showing the structure of another cell culture chamber according to this embodiment, and FIG. 12 is a sectional view taken along the line XI-XI of FIG. 11. Note that the openings 13 are not necessarily formed. As shown in FIGS. 3 and 4, the four sides of each of the microchambers 11 may be entirely surrounded by the side walls 12. Here, FIG. 3 is a plane view showing the structure of another cell culture chamber according to this embodiment, and FIG. 4 is a sectional view taken along the line IV-IV of FIG. 3.

Figure 5:
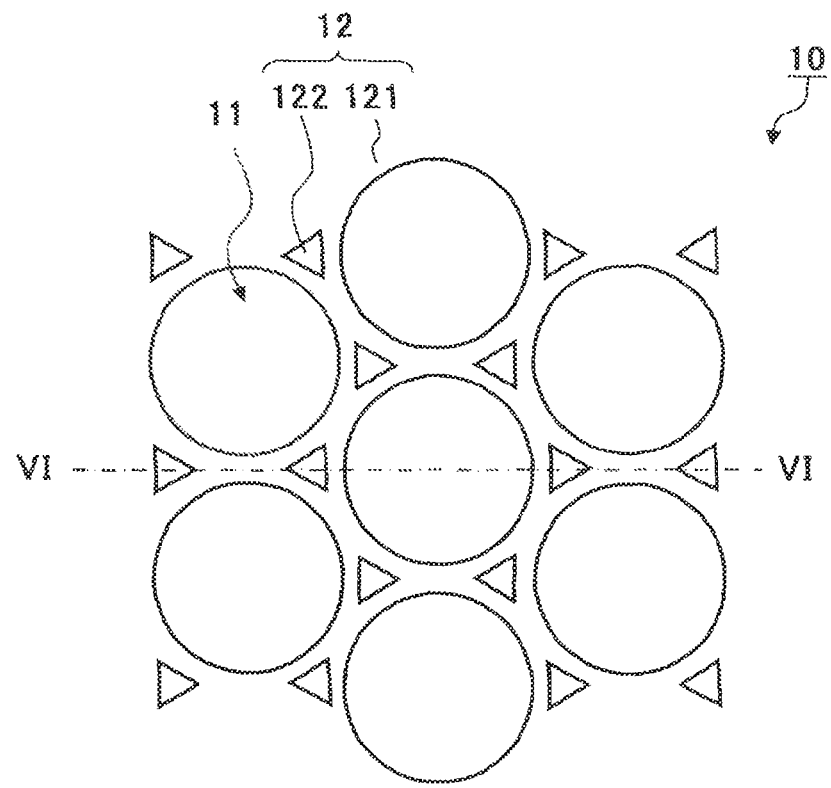
FIG. 5 is a plane view showing the structure of a cell culture chamber according to an embodiment of the present invention.
Figure 6:
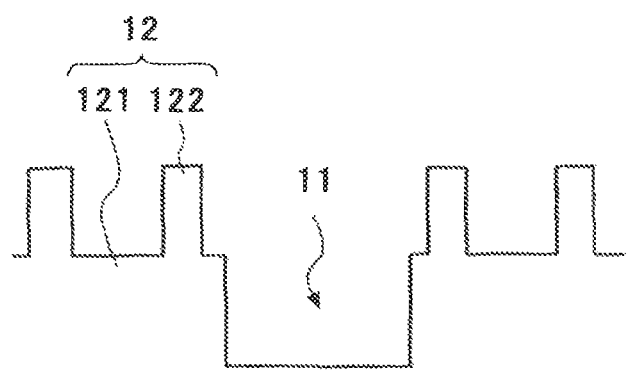
FIG. 6 is a sectional view showing the structure of the cell culture chamber according to an embodiment of the present invention.

Also, as shown in FIGS. 5 and 6, the microchambers 11 having a circular shape may be entirely surrounded by first side walls 121, and second side walls 122 may be formed on the first side walls 121. That is, the first side walls 121 and the second side walls 122 constitute the side walls (convex portions) 12 of a multi-stage structure. Here, FIG. 5 is a plane view showing the structure of another cell culture chamber according to this embodiment, and FIG. 6 is a sectional view taken along the line VI-VI of FIG. 5.

A method for forming the concave-convex pattern on the cell culture chamber of the present invention is not particularly limited, but methods such as transfer molding using a mold, three-dimensional stereolithography, precision machining, wet etching, dry etching, laser processing, and electrical discharge machining may be employed. It is preferable to appropriately select these production methods in view of the intended use, required processing accuracy, costs, and the like of the cell culture chamber.

As a specific example of the transfer molding method using a mold, a method for forming the concave-convex pattern by resin molding using a metal structure as a mold may be employed. This method is preferred because it is capable of reproducing the shape of the metal structure on a resin as the concave-convex pattern with a high transcription rate, and because the raw material cost can be reduced by using a general-purpose resin material. Such a method using a mold of a metal structure is superior in terms of low cost and achieving satisfactorily high dimensional accuracy.

As methods of producing the metal structure, for example, plating treatment, precision machining, wet etching, dry etching, laser processing, and electrical discharge machining on a resist pattern produced by photolithography or a resin pattern produced by three-dimensional stereolithography may be employed. The methods may be appropriately selected in view of the intended use, required processing accuracy, costs, and the like.

As methods of forming the concave-convex pattern on a resin using the metal structure, which is obtained as described above, as a mold, injection molding, press molding, monomer casting, solvent casting, hot embossing, or roll transfer by extrusion molding may be employed, for example. It is preferable to employ injection molding in view of its productivity and transcription property.

Materials for forming the cell culture chamber of the present invention are not particularly limited as long as the materials have self-supporting properties. For example, synthetic resin, silicon, or glass may be employed. A transparent synthetic resin is preferably used as a material in view of costs and cell visibility under microscopical observation. Examples of the transparent synthetic resin include acrylic resins such as polymethylmethacrylate or methyl methacrylate-styrene copolymer, styrene resin such as polystyrene, olefin resin such as cycloolefin, ester resins such as polyethylene terephthalate and polylactic acid, silicone resin such as polydimethylsiloxane, and polycarbonate resin. These resins may contain various additives such as colorant, dispersing agent, and thickening agent, unless the transparency is impaired.

In the cell culture chamber of the present invention, surface treatment may be performed on the surface side of the concave-convex pattern and a modified layer and/or a coating layer may be formed for the purpose of improving the hydrophilic properties, biocompatibility, cellular affinity, and the like of the chamber surface. A method for forming the modified layer is not particularly limited unless a method with which the self-supporting properties are impaired and a method causing extreme surface roughness of 10 μm or more are employed. Methods, for example, chemical treatment, solvent treatment, chemical treatment such as introduction of a graft polymer by surface graft polymerization, physical treatment such as corona discharge, ozone treatment, or plasma treatment may be employed. In addition, though a method for forming the coating layer is not particularly limited, methods, for example, dry coating such as sputtering or vapor deposition and wet coating such as inorganic material coating or polymer coating may be employed. In order to inject a culture solution without mixing air bubbles therein, it is desirable to impart the hydrophilic properties to the surface of the concave-convex pattern. As a method for forming a uniform hydrophilic membrane, inorganic vapor deposition is preferably employed.

When the cellular affinity is taken into consideration, it is more preferable to coat cytophilic proteins such as collagen and fibronectin, for example. In order to coat a collagen aqueous solution or the like uniformly, it is preferable to perform the coating after the above-mentioned hydrophilic membrane is formed. In cell culture, in general, it is desirable to culture cells on an extracellular matrix surface by replicating the in vivo environment. Accordingly, it is particularly preferable to dispose an organic film made of extracellular matrix suitable for cultured cells after an inorganic hydrophilic membrane is uniformly formed as described above.

In a cell culture method of the present invention, an appropriate number of cells need to be seeded so that the cells are arranged exclusively within the microchambers for culturing cells and morphologies and functions similar to those in vivo are developed within the space. A cell seeding density of $1.0 \times 10^4$ to $1.0 \times 10^6$ cells/cm$^2$ is preferably used. When each microchamber is a square which is 200 μm on a side, for example, a cell seeding density of $5.0 \times 10^4$ to $5.0 \times 10^5$ cells/cm$^2$ is preferably used. Under such conditions, a cell mass having a diameter of 30 to 200 μm can be obtained.

Mode for the Invention 1

Next, examples of the cell culture chamber according to the present invention will be described, but the present invention is not limited to these examples.

<Preparation of Liver Cells>

Liver cells of a primary rat for use in culture were prepared in a manner as described below. A surflow indwelling needle was inserted into the portal vein of a 6-week-old Wistar rat, and blood removal was performed by causing an EDTA-containing solution to flow. Then, a collagenase solution was perfused. After that, the liver treated by the collagenase solution was immersed in a culture solution, and the cells were dispersed by pipetting using a measuring pipette. The cell suspension was cleaned three times to remove cells other than the cells, and isolated cells were used for culture.

<Culture Method>

A culture solution for use in culture was prepared in a manner as described below.

A culture medium of DMEM/F12 was added with 10% fetal bovine serum, 1 μg/ml insulin, $1 \times 10^{-7}$ M dexamethasone, 10 mM nicotinamide, 2 mM L-glutamine, 50 μm β-mercaptoethanol, 5 mM HEPES, 59 μg/ml penicillin, 100 μg/ml streptomycin, 25 ng/ml HGF, and 20 ng/ml EGF.

On a base material having a concave-convex pattern, liver cells were seeded at a density of $1.0 \times 10^5$ cells/cm$^2$ and were cultured for a predetermined period of time with 5% CO$_2$ and at 37° C. Further, 0.5 mL fresh culture medium having the same composition was used, and the culture medium was changed every day or every two days.

EXAMPLE 1

A pattern which has the shape of the concave-convex pattern as shown in FIG. 3 and which has dimensions of a=100 um, b=10 um, and c=50 um was produced by photolithography, and Ni electrolytic plating was carried out to obtain a mold having a corresponding concave-convex shape. Pattern transcription was performed on polystyrene by hot embossing with the mold, and a resin base material having the above-mentioned dimensions was produced. A silicon dioxide film was formed with a thickness of 100 nm on the surface of the resin base material by vacuum deposition, and γ-ray sterilization was carried out to obtain the base material having the concave-convex pattern. Liver cells were cultured on the concave-convex base material.

COMPARATIVE EXAMPLE 1

A pattern which has the shape of the concave-convex pattern as shown in FIG. 3 and which has dimensions of a=100 um, b=20 um, and c=50 um was produced by photolithography, and Ni electrolytic plating was carried out to obtain a mold having a corresponding concave-convex shape. Pattern transcription was performed on polystyrene by hot embossing with the mold, and a resin base material having the above-mentioned dimensions was produced. A silicon dioxide film was formed with a thickness of 100 nm on the surface of the resin base material by vacuum deposition, and γ-ray sterilization was carried out to obtain the base material having the concave-convex pattern. Liver cells were cultured on the concave-convex base material.

Figure 7:
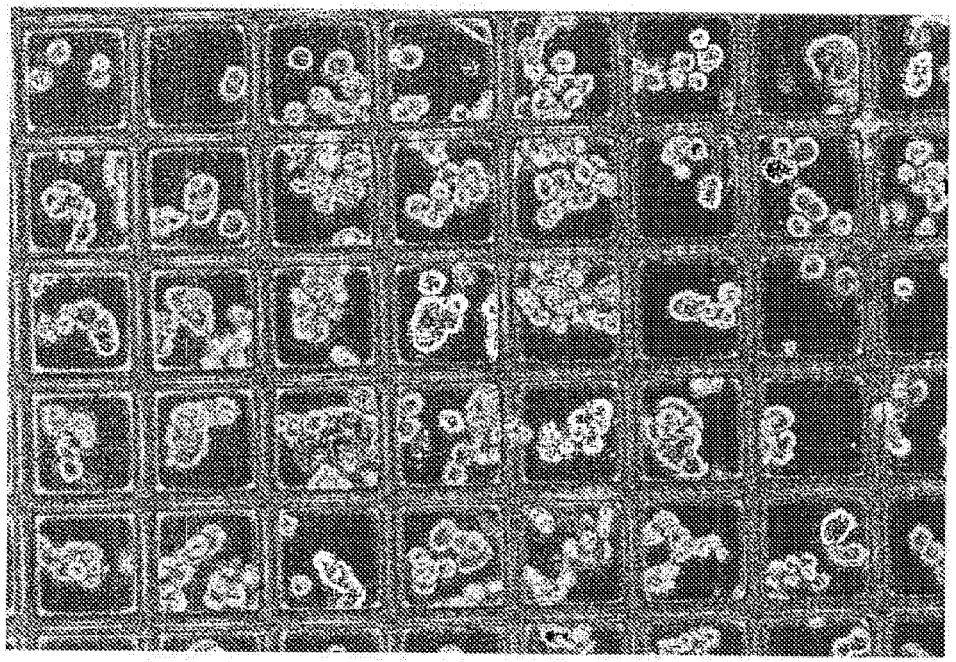
FIG. 7 is an optical microscope image of cultured cells in a cell culture chamber according to Example 1.
Figure 8:
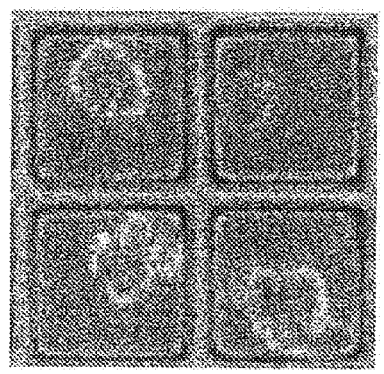
FIG. 8 is an optical microscope image of cultured cells in the cell culture chamber according to Example 1.

FIG. 7 is an optical microscope photograph showing a state after cells were seeded under the conditions of Example 1 and the cells were cultured for four hours. FIG. 8 is an optical microscope photograph showing a state after the cells were cultured for four days. The cells are not adhered to the upper surfaces of the convex portions that partition the culture spaces, and the cells are successfully cultured exclusively within the concave portions that are original culture spaces. As a result, an intercellular network could be constructed in the culture space and the functions similar to those in vivo could be developed.

Figure 9:
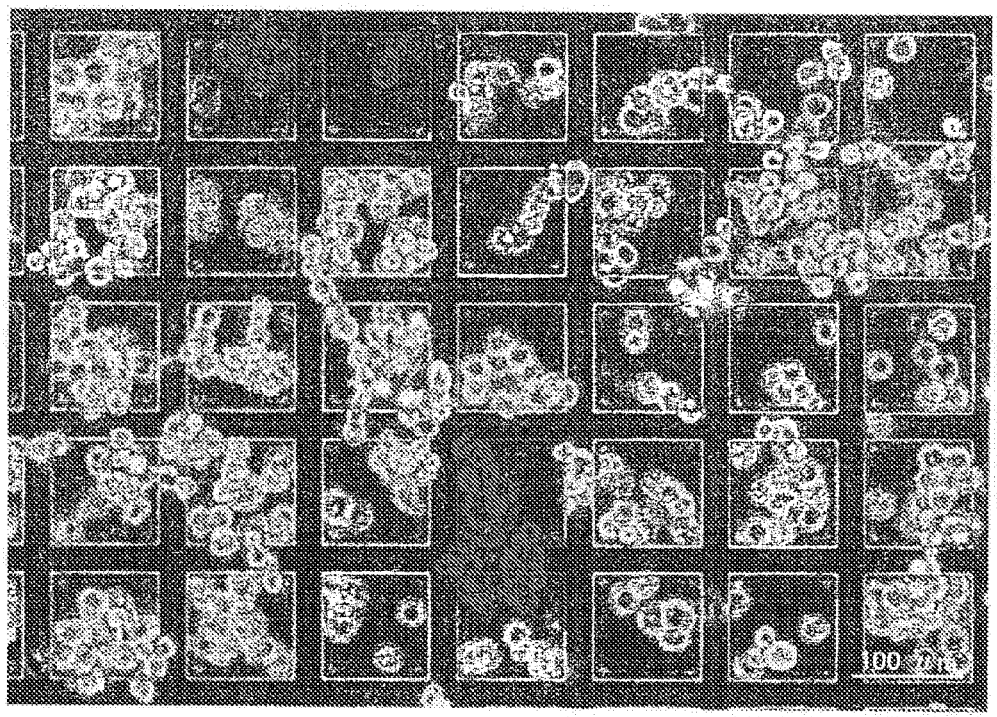
FIG. 9 is an optical microscope image of cultured cells in a cell culture chamber according to Comparative Example 1.
Figure 10:
FIG. 10 is an optical microscope image of cultured cells in the cell culture chamber according to Comparative Example 1.

FIG. 9 is an optical microscope photograph showing a state after cells were seeded under the conditions of Comparative Example 1 and the cells were cultured for four hours. FIG. 10 is an optical microscope photograph showing a state after the cells were cultured for four days. The cells are adhered also to the upper surfaces of the convex portions that partition the culture spaces, and were cultured thereon. Additionally, the adjacent culture spaces could not be distinctly partitioned, and the cells could not be cultured exclusively within the culture spaces. As a result, an intercellular network could not be constructed in the culture spaces, and the functions similar to those in vivo could not be developed.

EXAMPLE 2

A pattern which has the shape of the concave-convex pattern as shown in FIGS. 11 and 12 and which has dimensions of a=80 um, b=15 um, and c=50 um was produced by photolithography, and Ni electrolytic plating was carried out to obtain a mold having a corresponding concave-convex shape. Pattern transcription was performed on polystyrene by hot embossing with the mold, and a resin base material having the above-mentioned dimensions was produced. A silicon dioxide film was formed with a thickness of 100 nm on the surface of the resin base material by vacuum deposition, and γ-ray sterilization was carried out to obtain the base material having the concave-convex pattern. Liver cells were cultured on the concave-convex base material.

Figure 13:
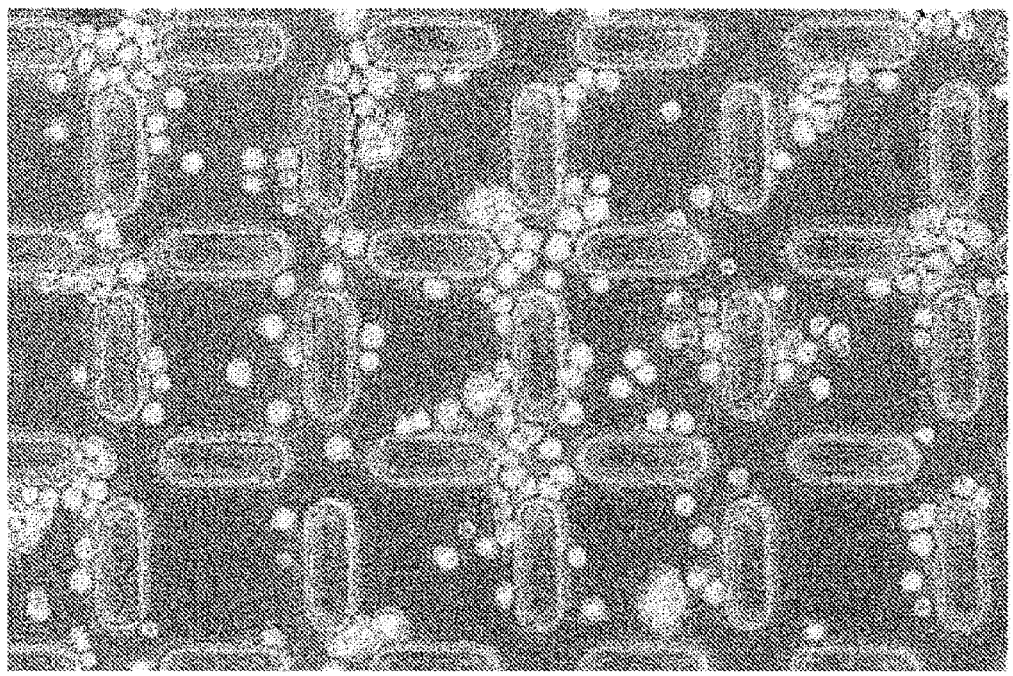
FIG. 13 is an optical microscope image of cultured cells in a cell culture chamber according to Example 2.

FIG. 13 is an optical microscope photograph showing a state after cells were seeded under the conditions of Example 2 and the cells were cultured for four hours. The cells are not adhered to the upper surfaces of the convex portions that partition the culture spaces, and the cells are successfully cultured exclusively within the concave portions that are original culture spaces. As a result, an intercellular network could be constructed in the culture spaces and the functions similar to those in vivo could be developed.

The invention claimed is:

1. A cell culture method for culturing cells only within microchambers, the method comprising:
   injecting cells into the microchambers formed in a cell culture chamber, and
   culturing the cells only within the microchambers, wherein the cells do not adhere to upper surfaces of convex portions,
   wherein the cell culture chamber comprises a plurality of microchambers formed on a surface of the cell culture chamber, and wherein the convex portions that partition the microchambers adjacent to one another are formed such that cells are contained in the microchambers, thereby preventing the cells from adhering to the upper surfaces of the convex portions,
   wherein each of the upper surfaces of the convex portions of the cell culture chamber has a short side width of from 0.5 to 15 μm, and each of the convex portions has a height more than three times of the short side width, and
   wherein the cells are liver cells.

2. The cell culture method according to claim 1, wherein the convex portions have a multi-stage structure and the cells do not adhere to an upper surface of each stage during culturing.

3. The cell culture method according to claim 1, wherein each of the convex portions has a height of from 30 to 300 μm.

4. The cell culture method according to claim 1, wherein 50% or more of an upper portion in a height direction of the convex portions has an angle of 80° to 90° formed between a bottom surface of the microchamber and each side surface of the convex portions.

5. The cell culture method according to claim 1, wherein each of the microchambers has a bottom surface area of $6.25 \times 10^{-4}$ mm$^2$ to 0.563 mm$^2$.

6. The cell culture method according to claim 1, wherein a bottom surface of each of the microchambers has a major axis which is 1 to 1.5 times a minor axis of the bottom surface.

7. The cell culture method according to claim 1, wherein a bottom surface of each of the microchambers has a major axis which is 1.5 to 50 times a minor axis of the bottom surface, and migration properties of cells are evaluated.

8. The cell culture method according to claim 1, wherein the microchambers communicate with at least one adjacent microchamber.

9. The cell culture method according to claim 8, wherein an opening for allowing the microchambers to communicate with the at least one adjacent microchamber has a width of 1 to 25 μm.

10. The cell culture method according to claim 1, wherein an area having micropatterns is surface treated.

11. The cell culture method according to claim 10, wherein an integrated layer film formed by the surface treatment has two or more layers comprising at least one layer of an inorganic film and at least one layer of an organic film.

* * * * *

UNITED STATES PATENT AND TRADEMARK OFFICE
CERTIFICATE OF CORRECTION

PATENT NO. : 8,415,157 B2
APPLICATION NO. : 13/229087
DATED : April 9, 2013
INVENTOR(S) : Go Tazaki et al.

It is certified that error appears in the above-identified patent and that said Letters Patent is hereby corrected as shown below:

On the title page, Item (54) and in the specification, Column 1, the title should read:

-- CELL CULTURE CHAMBER AND CELL CULTURE METHOD --

Signed and Sealed this
Eighteenth Day of June, 2013

Teresa Stanek Rea
*Acting Director of the United States Patent and Trademark Office*